United States Patent
Hennessey

(10) Patent No.: US 8,764,705 B2
(45) Date of Patent: Jul. 1, 2014

(54) BALLOON WITH INTEGRAL SEGMENTED DILATION ELEMENTS

(75) Inventor: Eric R. Hennessey, Lewisville, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 13/696,473

(22) PCT Filed: Apr. 29, 2011

(86) PCT No.: PCT/US2011/034460
§ 371 (c)(1),
(2), (4) Date: Nov. 6, 2012

(87) PCT Pub. No.: WO2011/139878
PCT Pub. Date: Nov. 10, 2011

(65) Prior Publication Data
US 2013/0053768 A1  Feb. 28, 2013

Related U.S. Application Data

(60) Provisional application No. 61/332,384, filed on May 7, 2010.

(51) Int. Cl.
*A61M 25/10* (2013.01)

(52) U.S. Cl.
USPC .............. 604/103.08; 604/96.01; 604/103.09; 604/103.07; 264/523; 264/525

(58) Field of Classification Search
USPC .............. 604/69.01, 103.06, 103.07, 103.08, 604/103.09, 191, 192, 194, 96.01; 264/523, 264/525
See application file for complete search history.

(56) References Cited

U.S. PATENT DOCUMENTS

| | | |
|---|---|---|
| 5,178,625 A | 1/1993 | Groshong |
| 5,807,326 A | 9/1998 | O'Neill et al. |
| 5,919,200 A | 7/1999 | Stambaugh et al. |
| 6,562,062 B2 | 5/2003 | Jenusaitis et al. |
| 6,632,231 B2 | 10/2003 | Radisch, Jr. |
| 6,942,680 B2 * | 9/2005 | Grayzel et al. ............... 606/194 |
| 7,008,438 B2 * | 3/2006 | O'Brien ....................... 606/159 |
| 7,172,609 B2 | 2/2007 | Radisch, Jr. |
| 7,270,673 B2 | 9/2007 | Yee et al. |
| 7,279,002 B2 | 10/2007 | Shaw et al. |
| 7,291,158 B2 | 11/2007 | Crow et al. |
| 7,303,572 B2 | 12/2007 | Melsheimer et al. |
| 7,494,497 B2 | 2/2009 | Weber |
| 2004/0143287 A1 | 7/2004 | Konstantino et al. |
| 2008/0300610 A1 | 12/2008 | Chambers |
| 2009/0192537 A1 | 7/2009 | O'Brien |

FOREIGN PATENT DOCUMENTS

WO  WO 2009/114425 A1  9/2009

OTHER PUBLICATIONS

Search Report for related PCT Application No. PCT/US2011/034460 mailed Aug. 4, 2011.

* cited by examiner

*Primary Examiner* — Laura Bouchelle
(74) *Attorney, Agent, or Firm* — Brinks Gilson & Lione

(57) ABSTRACT

A balloon and method of making a balloon catheter is provided. The balloon for the balloon catheter may be made by slicing through an integral dilation element on a parison (10). The parison may then be stretched to spread the slices to form wider gaps (20). The gaps define separate dilation element segments (14), which may make the balloon more flexible.

20 Claims, 3 Drawing Sheets

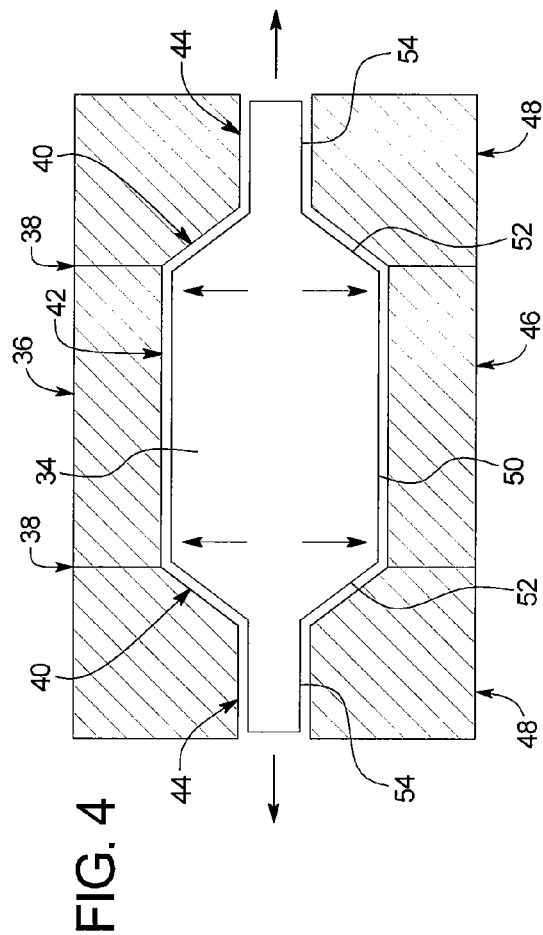
FIG. 4
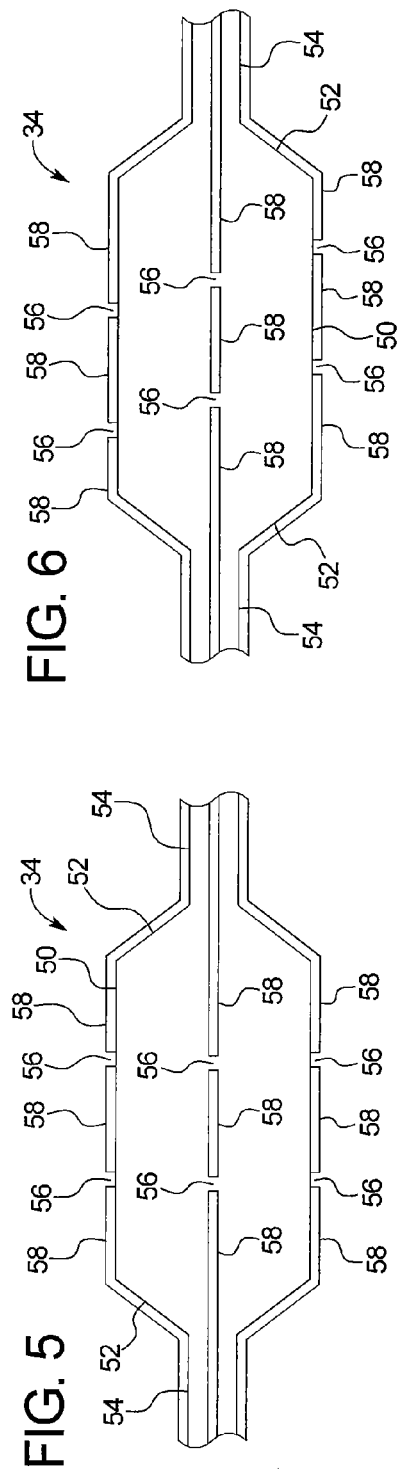
FIG. 6
FIG. 5

BALLOON WITH INTEGRAL SEGMENTED DILATION ELEMENTS

This application is a National Stage of International Application PCT/US2011/034460 filed Apr. 29, 2011, which claims the benefit of the filing date under 35 U.S.C. §119(e) of Provisional U.S. Patent Application Ser. No. 61/332,384 filed May 7, 2010. The entirety of both applications is hereby incorporated by reference.

BACKGROUND

The present invention relates generally to medical devices and particularly to a balloon catheter with dilation elements along the exterior surface of the balloon.

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow).

Although balloon catheters are used in many other procedures as well, vascular angioplasty using a balloon catheter has drawn particular attention from the medical community because of the growing number of people suffering from vascular problems associated with arterial stenosis. This has lead to an increased demand for medical procedures to treat such problems. The widespread frequency of vascular problems may be due to a number of societal changes, including the tendency of people to exercise less while eating greater quantities of unhealthy foods, in conjunction with the fact that people generally now have longer life spans than previous generations. Angioplasty procedures have become a popular alternative for treating arterial stenosis because angioplasty procedures are considerably less invasive than other alternatives. As an example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for vascular treatments, the medical community has turned to angioplasty procedures, in combination with stenting and other procedures, to avoid the problems associated with traditional open surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg arteries) and threading the catheter to the narrowed part of the artery to be treated. During this stage, the balloon is uninflated and collapsed onto the shaft of the catheter in order to present a low profile which may be passed through the vasculature. Once the balloon is positioned at the narrowed part of the artery, the balloon is expanded by pumping a mixture of saline and contrast solution through the catheter to the balloon. As a result, the balloon presses against the inner wall of the artery to dilate it. If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the body. If a stent is mounted on the balloon of the catheter, the stent is left permanently implanted in its expanded state at the desired location in the artery to provide a support structure that prevents the artery from collapsing back to its pre-dilated condition. On the other hand, if the balloon catheter is not adapted for delivery of a stent, either a balloon-expandable stent or a self-expandable stent may be implanted in the dilated region in a follow-up procedure. Although the treatment of stenosed arteries is one common example where balloon catheters have been used, this is only one example of how balloon catheters may be used and many other uses are also possible.

One problem that may be encountered with conventional angioplasty techniques is the proper dilation of stenosed regions that are hardened and/or have become calcified. Stenosed regions may become hardened for a variety of reasons, such as the buildup of atherosclerotic plaque or other substances. Hardened regions of stenosis can be difficult to completely dilate using conventional balloons because hardened regions tend to resist the expansion pressures applied by conventional balloon catheters. One solution that has been offered for dilating hardened stenoses is special balloon catheters with dilation wires or beads that extend along the length of the balloon. The dilation wires and/or beads focus that dilation pressure of the balloon onto the narrower contact area between the dilation wire or bead and the vessel wall. As a result, the increased, focused pressure may crack and/or break up the hardened stenosis, thereby allowing the vessel lumen to be expanded.

Many balloon catheters with dilation wires or beads are manufactured by attaching a separate wire or other material to the exterior of the balloon. This may be accomplished, for example, by using adhesives to bond the dilation element to the balloon. This approach has several advantages, including being able to use an optimized material and shape for the dilation element and manufacturing processes that are relatively straightforward. However, separate dilation elements can be disadvantageous because there may be concern by physicians that the dilation element could break loose from the surface of the balloon. Thus, dilation elements that are integral with the balloon may be preferable despite some of the advantages of separate dilation elements.

Another concern with balloons that have dilation elements along the exterior of the balloon is that the dilation elements tend to make the balloon less flexible. Flexibility is particularly important for balloon catheters because they are frequently used to traverse narrow passageways with tortuous paths. Accordingly, the inventor believes it would be desirable to provide a balloon catheter with integral dilation elements that are flexible.

SUMMARY

A balloon catheter is described with integral dilation element segments that are separated from each other by a gap. The dilation element segments may be made by cutting through an integral dilation element formed on the exterior surface of a parison. The parison may then be stretched to widen the cuts to form gaps separating multiple dilation element segments.

The invention may include any of the following aspects in various combinations and may also include any other aspect described below in the written description or in the attached drawings.

A method of forming a balloon for a balloon catheter, comprising: extruding a parison having a uniform shape along an entire length thereof, the parison comprising a central opening and a dilation element extending from an exterior surface of the parison;

cutting through a portion of the dilation element;

heating and stretching at least a portion of the parison, segments of the dilation element defined by the cutting thereby separating from each other to form gaps between the segments; and heating the parison inside a mold and pressurizing the central opening, the parison thereby expanding against the mold to form a balloon.

The method wherein the cutting comprises making a single blade slice through the portion, a width of the cutting thereby being approximately the same as a width of a cutting blade.

The method wherein the width of the cutting blade is about 0.005" to about 0.015".

The method wherein the cutting comprises cutting about 25% to about 75% through a total height of the dilation element.

The method wherein the parison comprises more than one of the dilation element circumferentially spaced around the exterior surface, wherein all of the cutting comprises cutting longitudinally aligned cuts along the more than one of the dilation element.

The method wherein the parison comprises more than one of the dilation element circumferentially spaced around the exterior surface, wherein all of the cutting comprises cutting longitudinally staggered cuts along the more than one of the dilation element, none of the cuts thereby being longitudinally aligned with another cut on one of the circumferentially spaced dilation elements.

The method wherein the heating and stretching are done simultaneously with the heating of the parison and pressurizing the central opening.

The method wherein the parison is stretched a single time after the cutting.

The method wherein the stretching comprises stretching the portion of the parison less than twice a length of the portion before the stretching.

The method further comprising preforming the parison before the cutting to form an increased diameter middle region and reduced diameter end regions.

The method wherein the cutting comprises making a single blade slice through the portion, a width of the cutting thereby being approximately the same as a width of a cutting blade, and the cutting further comprising cutting about 25% to about 75% through a total height of the dilation element, the stretching comprising stretching the portion of the parison less than twice a length of the portion before the stretching.

The method wherein the parison comprises more than one of the dilation element circumferentially spaced around the exterior surface, wherein all of the cutting comprises cutting longitudinally staggered cuts along the more than one of the dilation element, none of the cuts thereby being longitudinally aligned with another cut on one of the circumferentially spaced dilation elements, the heating and stretching being done simultaneously with the heating of the parison and pressurizing the central opening and the parison being stretched a single time after the cutting, and further comprising preforming the parison before the cutting to form an increased diameter middle region and reduced diameter end regions.

The method wherein the width of the cutting blade is about 0.005" to about 0.015" and the cutting comprises cutting about 25% to about 75% through a total height of the dilation element, the parison being stretched a single time after the cutting, and further comprising preforming the parison before the cutting to form an increased diameter middle region and reduced diameter end regions.

The method wherein the heating and stretching are done simultaneously with the heating of the parison and pressurizing the central opening, and the stretching comprising stretching the portion of the parison less than twice a length of the portion before the stretching.

A balloon catheter, comprising:
a balloon mounted on a catheter, the balloon configured to expand from a deflated state to an expanded state;
a plurality of dilation element segments disposed along a length of an exterior surface of the balloon and integrally formed therewith, the dilation element segments generally being circumferentially aligned with each other;
wherein the dilation element segments are spaced away from each other by a gap that is less than 0.060".

The balloon catheter wherein the balloon comprises more than one of the plurality of dilation element segments circumferentially spaced around the exterior surface, wherein all of the gaps are longitudinally aligned with corresponding gaps in each of the plurality of dilation element segments.

The balloon catheter wherein the balloon comprises more than one of the plurality of dilation element segments circumferentially spaced around the exterior surface, wherein all of the gaps are longitudinally staggered from corresponding gaps in each of the plurality of dilation element segments, none of the gaps thereby being longitudinally aligned with another gap on one of the circumferentially spaced plurality of dilation element segments.

The balloon catheter wherein the dilation element segments comprise a neck portion and a head portion, at least part of the neck portion extending across each of the gaps.

The balloon catheter wherein the balloon comprises more than one of the plurality of dilation element segments circumferentially spaced around the exterior surface, wherein all of the gaps are longitudinally staggered from corresponding gaps in each of the plurality of dilation element segments, none of the gaps thereby being longitudinally aligned with another gap on one of the circumferentially spaced plurality of dilation element segments, and wherein the dilation element segments comprise a neck portion and a head portion, at least part of the neck portion extending across each of the gaps.

BRIEF DESCRIPTION OF SEVERAL VIEWS OF THE DRAWINGS

The invention may be more fully understood by reading the following description in conjunction with the drawings, in which:

FIG. 4 is a side view of a balloon being blow molded in a mold;
FIG. 5 is a side view of a balloon with aligned gaps between segments of dilation elements;
FIG. 6 is a side view of a balloon with staggered gaps between segments of dilation elements.

DETAILED DESCRIPTION

Figure 1:
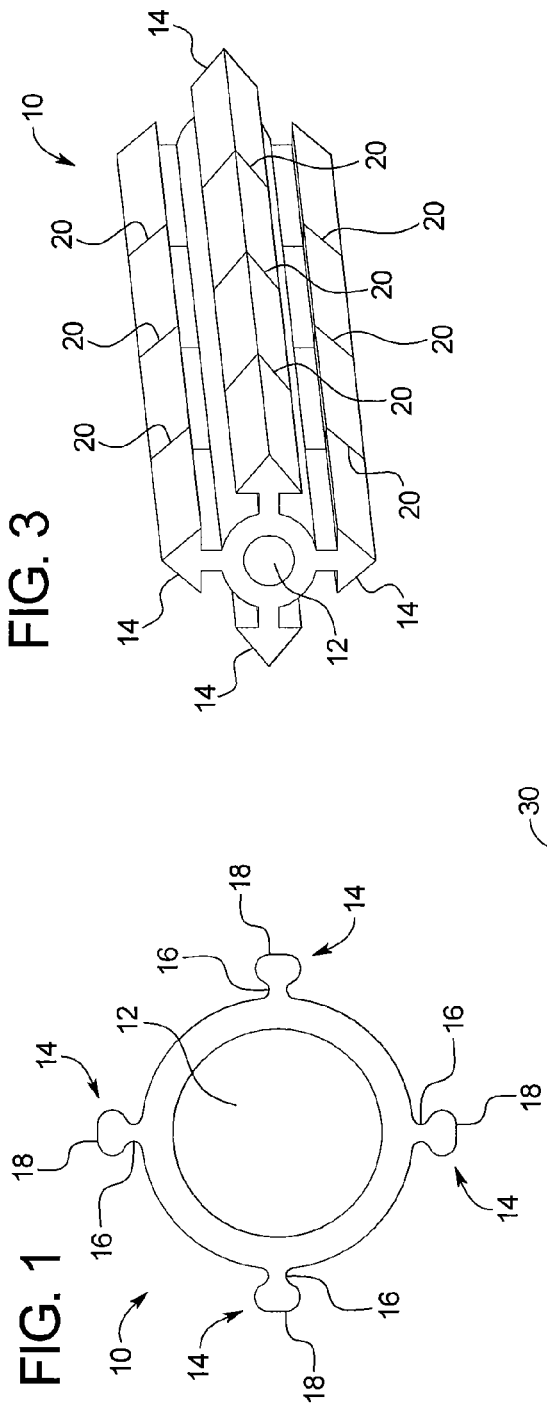
FIG. 1 is an end view of a parison.

Referring now to the figures, and particularly to FIG. 1, a parison 10 is shown. The parison 10 may be formed by continuously extruding a polymer material, such as nylon, through a mold. Thus, each of the structures of the extruded parison 10 are integral with each other and extend along the entire length of the extruded parison 10. The extruded parison 10 may have a central opening 12 that is used for blow molding the parison 10 as described below. The central opening 12 will form the inner lumens of the neck regions 54, which are attached to a catheter 60, and will also form the interior of the balloon 34, which allows the balloon 34 to expand from a deflated state to an expanded state. The parison 10 may also include a plurality of integral dilation elements 14 extending along the entire length of the parison 10. Although the size and shape of the dilation elements 14 may be altered slightly by subsequent manufacturing steps, such as blow molding as described below, it is desirable for the width of the neck portion 16 of the dilation element 14 to be about 0.010" to about 0.020" and the height of the neck portion 16 to be about 0.010" to about 0.025" on the finished balloon 34. It is also desirable for the width of the head portion 18 of the dilation element 14 to be about 0.015" to about 0.030" and the height of the head portion 18 to be about 0.010" to about 0.020". In general, however, the width of the neck portion 16 is less than the width of the head portion 18.

Figure 2:
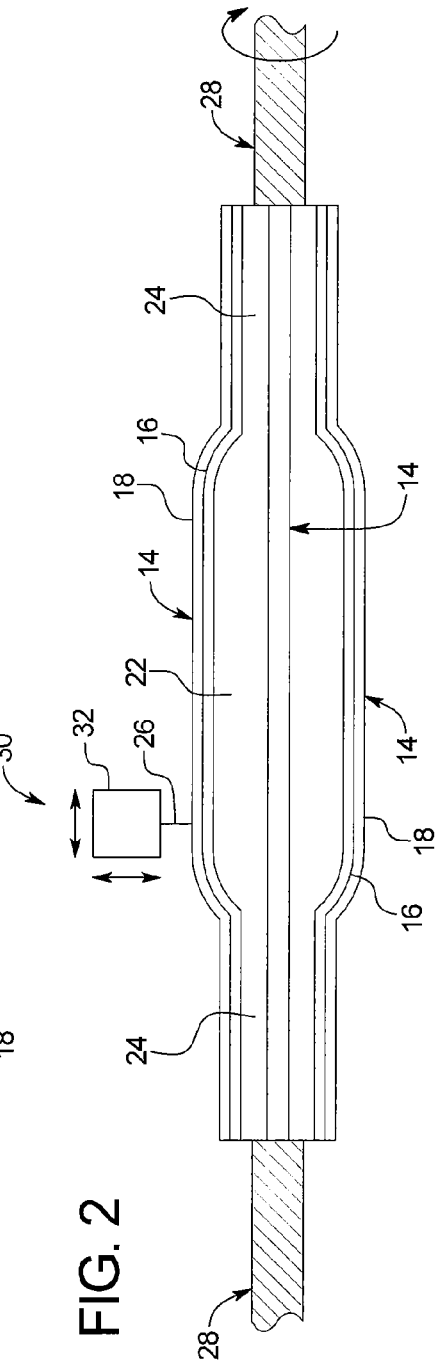
FIG. 2 is schematic view of a machine for cutting dilation elements.

As shown in FIG. 2, each of the dilation elements 14 may be cut with a plurality of slices 20 before blow molding the parison 10 into a balloon 34. As shown, it may be preferable to initially preform the parison 10 before cutting the dilation elements 14 so that the middle region 22 has an increased diameter and the end regions 24 have a reduced diameter compared to the middle region 22. The initial preforming process may be achieved by heating the middle region 22 without heating the end regions 24 while the parison 10 is in a tube with a slightly larger diameter than the parison 10. Pressure may then be applied to the center opening 12 so that the middle region 22 expands until it is restrained by the tube. The entire length of the parison 10 may also be heated while the parison 10 is in a mold with reduced diameter end sections for the end regions 24 of the parison 10 and an increased diameter middle section for the middle region 22 of the parison 10. Alternatively, one end 24 of the parison 10 may be heated without heating the middle region 22 of the parison 10. The heated end 24 of the parison 10 may be pulled to stretch it without causing the middle region 22 to be stretched. The other end 24 may then be heated and stretched in a similar manner. One advantage of slightly increasing the diameter of the middle region 22 before cutting the dilation elements 14 is that the increased diameter middle region 22 can be used to longitudinally position the parison 10 in the blow molding mold 36. This may allow the cuts 20 to be more precisely positioned on the parison 10 relative to the final balloon 34, which will result in more accurate placement of the dilation element segments 58 and gaps 56 described below.

Figure 3:
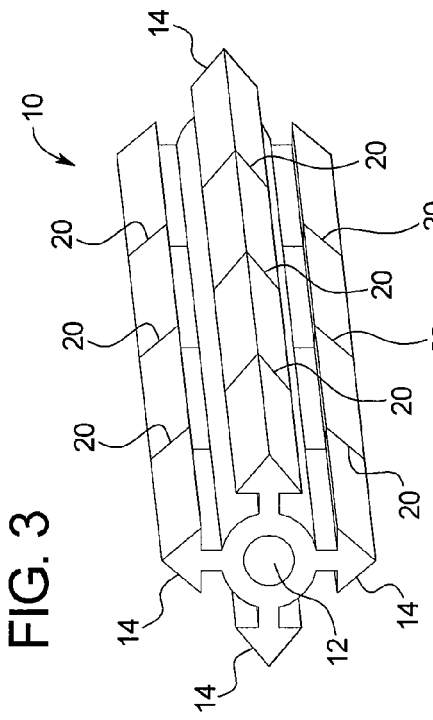
FIG. 3 is a perspective view of the parison.

The cuts 20, or slices 20, may be made with a single blade 26, such as a razor blade 26. Preferably, each of the cuts 20 is made by making a single slice 20 through a portion of the dilation element 14. Thus, where the width of the blade 26 is preferably about 0.005" to about 0.015", the corresponding width of the slice 20 through the dilation element 14 is also about 0.005" to about 0.015". The depth of the slice 20 through the dilation element 14 is preferably about 25% to about 75% of the total height of the dilation element 14, including the head portion 18 and the neck portion 16. Because of the thin wall of the working diameter region 50 of the finished balloon 34, it is particularly important that the cuts 20 do not penetrate any part of the main body of the parison 10. For example, in a typical balloon 34, the wall thickness of the working diameter region 50 may be about 0.001" to about 0.002". Because of the especially thin wall thickness of the balloon 34, any cut into the main body could cause a rupture in the balloon 34 during use. Thus, it is preferred that at least part of the neck portion 16 of the dilation element 14 extends across each of the gaps 56 in the finished balloon 34. By contrast, the neck regions 54 of the balloon 34 typically have a thickness of about 0.008" to about 0.015". Thus, removal of the dilation elements 14 from the neck regions 54 is somewhat less sensitive than slicing through the dilation elements 14 along the working diameter region 50. In order to control the placement and depth of the cuts 20, it is preferred that the parison 10 is mounted on a mandrel 28. The mandrel 28 may be mounted in a computer-controlled machine 30 that does the cutting. Thus, the blade 26 is preferably attached to a head 32 that is capable of traversing longitudinally and traveling up and down. The mandrel 28 is preferably rotatable in response to the computer control. As shown in FIG. 3, the cutting machine 30 makes a plurality of slices 20 through each of the dilation elements 14. As described below, the placement of the slices 20 is determined by the desired placement of the dilation element segments 58 and gaps 56 on the finished balloon 34.

As shown in FIG. 4, after the parison 10 has been extruded, the parison 10 is blow molded into the shape of a balloon 34. The balloon 34 may be blow molded inside an open cavity in the mold 36 by applying pressure inside the center opening 12 of the parison 10 and heating the parison 10 and/or mold 36. While the mold 36 may take various forms, a three-piece mold 36 may be desirable. The three-piece mold 36 may be split in two places 38 at the transition between the tapered regions 40 and the working diameter 42. The parison 10 may be inserted into the mold 36 by separating one or more of the pieces of the mold 36 and inserting one end 24 of the parison 10 through one of the neck regions 44 in the mold 36. The working diameter piece 46 and/or the other neck piece 48 may then be slid over the other end 24 of the parison 10. As shown, the blow molded balloon 34 has a working diameter region 50, tapered regions 52 that extend from each end of the working diameter region 50, and neck regions 54 that extend from the end of each of the tapered regions 52. If desired, cavities may be provided in the mold 36 to accommodate the dilation elements 14 of the extruded parison 10. The cavities may be sized to provide sufficient clearance for the dilation elements 14 during the blow molding process so that the size and shape of the dilation elements 14 do not change during the blow molding. Alternatively, cavities may be provided for the dilation elements 14 with a size that reforms the dilation elements 14 from the size and shape of the extruded dilation elements 14.

Preferably, the parison 10 is also stretched during the blow molding process. Stretching the parison 10 during blow molding helps to form the balloon 34 into the tapered regions 40 and neck regions 44 of the mold 36 and helps achieve the desired wall thicknesses of the balloon 34. In addition, the stretching spreads the sliced cuts 20 to form larger gaps 56 in the dilation elements 14 as shown in FIGS. 5 and 6. However, the amount of stretching may be different along the length of the balloon 34. For example, the neck regions 54 and tapered regions 52 may be stretched more than the working diameter region 50. Preferably, the stretching of the working diameter region 50 is minimal so that the cuts 20 are only slightly magnified to form the desired gaps 56. In order to control the final size of the gaps 56, it is preferable that the parison 10 is stretched only one time after the cuts 20 are made through the dilation elements 14. It is also preferable that the single stretching step occur simultaneously with the blow molding process. However, it is possible that more than one stretching step could occur after the cutting step, and it is also possible that the stretching step could occur at a different time than the blow molding process. In any event, it is preferred that the amount of stretching of the working diameter region 50 be less than twice the length of the working diameter region 50 before the stretching. It is also preferable that the final size of the gaps 56 in the finished balloon 34 be about 0.010" to about 0.050", although the final size of the gaps 56 are preferably less than 0.060".

As shown in FIG. 5, the cuts 20 on different dilation elements 14 may be longitudinally aligned with each other. As a result, the dilation element segments 58 formed by the gaps 56 on circumferentially spaced away dilation elements 14 are longitudinally aligned with each other. This embodiment may be preferred because the cuts 20 are simpler to make since the blade 26 can be positioned near the parison 10 and the parison 10 can be rotated a full rotation to allow the blade 26 to cut through all of the dilation elements 14 at the same longitudinal position. Thus, in this embodiment, the dilation elements 14 need not be indexed to the cutting blade 26. This embodiment also provides a symmetrical arrangement of dilation element segments 58 that may be desirable for its uniform bending properties from side-to-side and uniform positioning of the dilation element segments 58.

As shown in FIG. 6, the cuts 20 on different dilation elements 14 may also be longitudinally staggered with respect to each other. As a result, the dilation element segments 58 formed by the gaps 56 on circumferentially spaced away dilation elements 14 are longitudinally staggered with respect to each other. Thus, in this embodiment, it is preferred that the gaps 56 on one dilation element 14 are not longitudinally aligned with any of the gaps 56 on the other dilation elements 14 that are circumferentially spaced away. This embodiment is likely to be somewhat more difficult to make because the blade 26 must travel longitudinally after each cut. However, with a computerized cutting machine 30 with conventional travel controls, sufficiently precise placement of the cuts 20 is possible. It is also important in this embodiment that the length of the blade 26 be less than the circumferential distance between the two circumferentially adjacent dilation elements 14 from the one being cut so that the blade 26 only cuts through a single dilation element 14 at a time. The dilation elements 14 must also be initially indexed to the cutting blade 26 to ensure that the cutting blade 26 is properly oriented circumferentially to the dilation elements 14. This embodiment may be preferred because the bending characteristics of the balloon 34 will be smoother along the length of the balloon 34. By comparison, the embodiment of FIG. 5 will tend to concentrate bending at discrete longitudinal locations where the gaps 56 are aligned with each other. However, in the embodiment of FIG. 6, the tendency to bend will be distributed more evenly along the length of the balloon 34 since the balloon 34 will tend to bend a slight amount at each of the longitudinal positions where there is a gap 56. The embodiment of FIG. 6, may also be less resistant to catching on other surfaces during use since the gaps 56 are not longitudinally aligned with each other and only one gap 56 is likely to catch on a surface at any particular time. Another advantage of the staggered gaps 56 is that during use in dilating a vascular stenosis two or more dilation element segments 58 will contact every longitudinal position of the stenosis. In other words, even at the longitudinal position of one of the gaps 56, where the gap 56 will prevent the dilation element 14 from contacting the vessel wall, at least two adjacent dilation element segments 58 will contact the vessel wall since the gaps 56 are not longitudinally aligned with each other. Still another advantage of the staggered design of FIG. 6 is that the longitudinal stretching of the balloon 34 during the blow molding process is not concentrated at discrete longitudinal positions. By contrast, one possible problem with the embodiment of FIG. 5 is that during stretching the parison 10 will stretch more where the gaps 56 are aligned with each other than at other longitudinal positions, since the dilation element segments 58 may resist stretching at all other longitudinal positions away from the gaps 56. This could cause the balloon wall to become thinner at the longitudinal position of the gaps 56 than along the rest of the balloon 34. However, in the embodiment of FIG. 6, the longitudinal stretching may be more evenly spread out along the length of the balloon 34 to minimize localized thinning of the wall thickness of the balloon 34.

Figure 7:
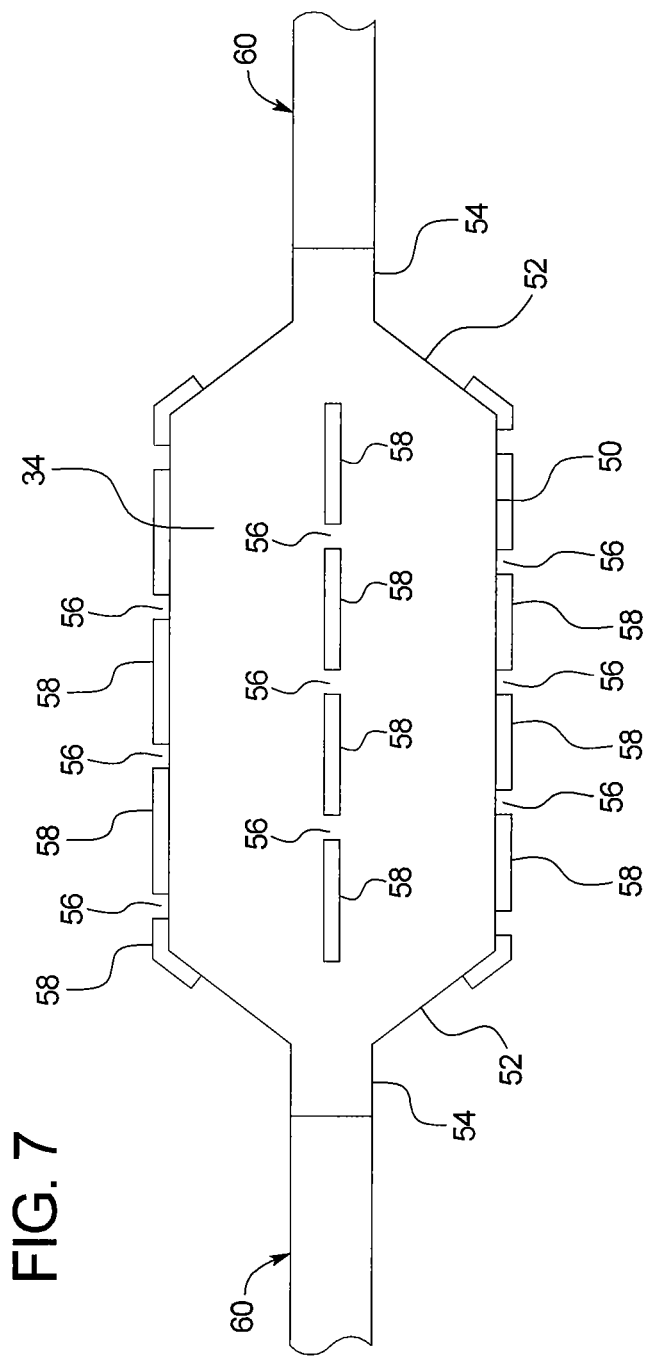
FIG. 7 is a side view of a balloon catheter with segmented dilation elements.

As shown in FIG. 7, after the parison 10 has been blow molded, the balloon 34 is cooled and removed from the mold 36. The balloon 34 is then mounted onto a catheter 60 by inserting the catheter 60 through the inner lumens of the neck regions 54 of the balloon 34. Preferably, the catheter 60 is bonded and sealed to the neck regions 54 of the balloon 34 by melt bonding. This may be accomplished by disposing heat shrink tubing over the neck regions 54 of the balloon 34. The heat shrink tubing, neck regions 54 and catheter 60 are then heated. The heat softens the neck regions 54 and the catheter 60 and causes the heat shrink tubing to shrink and squeeze the neck regions 54 and catheter 60 together. As a result, the neck regions 54 and catheter 60 melt together and adhere to each other when the heat shrink tubing, neck regions 54 and catheter 60 cool. In addition, any portions of the dilation elements 14 that remain on the neck regions 54 after removal are substantially reformed into the exterior surface of the neck regions 54 of the balloon 34 by the pressure of the heat shrink tubing and the softening caused by the heat. Preferably, the heat shrink tubing is removed from the neck regions 54 after the melt bonding. This provides a smooth attachment between the catheter 60 and the balloon 34 without any significant remnant of the dilation elements 34 along the neck regions 54.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A method of forming a balloon for a balloon catheter, comprising:
    extruding a parison having a uniform shape along an entire length thereof, said parison comprising a central opening and a dilation element extending from an exterior surface of said parison;
    cutting through a portion of said dilation element;
    heating and stretching at least a portion of said parison, segments of said dilation element defined by said cutting thereby separating from each other to form gaps between said segments; and
    heating said parison inside a mold and pressurizing said central opening, said parison thereby expanding against said mold to form a balloon.

2. The method according to claim 1, wherein said cutting comprises making a single blade slice through said portion, a width of said cutting thereby being approximately the same as a width of a cutting blade.

3. The method according to claim 2, wherein said width of said cutting blade is about 0.005" to about 0.015".

4. The method according to claim 1, wherein said cutting comprises cutting about 25% to about 75% through a total height of the dilation element.

5. The method according to claim 1, wherein said parison comprises more than one of said dilation element circumferentially spaced around said exterior surface, wherein all of said cutting comprises cutting longitudinally aligned cuts along said more than one of said dilation element.

6. The method according to claim 1, wherein said parison comprises more than one of said dilation element circumferentially spaced around said exterior surface, wherein all of said cutting comprises cutting longitudinally staggered cuts along said more than one of said dilation element, none of said cuts thereby being longitudinally aligned with another cut on one of said circumferentially spaced dilation elements.

7. The method according to claim 1, wherein said heating and stretching are done simultaneously with said heating of said parison and pressurizing said central opening.

8. The method according to claim 1, wherein said parison is stretched a single time after said cutting.

9. The method according to claim 1, wherein said stretching comprises stretching said portion of said parison less than twice a length of said portion before said stretching.

10. The method according to claim 1, further comprising preforming said parison before said cutting to form an increased diameter middle region and reduced diameter end regions.

11. The method according to claim 1, wherein said cutting comprises making a single blade slice through said portion, a width of said cutting thereby being approximately the same as a width of a cutting blade, and said cutting further comprising cutting about 25% to about 75% through a total height of the dilation element, said stretching comprising stretching said portion of said parison less than twice a length of said portion before said stretching.

12. The method according to claim 11, wherein said parison comprises more than one of said dilation element circumferentially spaced around said exterior surface, wherein all of said cutting comprises cutting longitudinally staggered cuts along said more than one of said dilation element, none of said cuts thereby being longitudinally aligned with another cut on one of said circumferentially spaced dilation elements, said heating and stretching being done simultaneously with said heating of said parison and pressurizing said central opening and said parison being stretched a single time after said cutting, and further comprising preforming said parison before said cutting to form an increased diameter middle region and reduced diameter end regions.

13. The method according to claim 1, wherein said width of said cutting blade is about 0.005" to about 0.015" and said cutting comprises cutting about 25% to about 75% through a total height of the dilation element, said parison being stretched a single time after said cutting, and further comprising preforming said parison before said cutting to form an increased diameter middle region and reduced diameter end regions.

14. The method according to claim 13, wherein said heating and stretching are done simultaneously with said heating of said parison and pressurizing said central opening, and said stretching comprising stretching said portion of said parison less than twice a length of said portion before said stretching.

15. The method according to claim 1, wherein each of said gaps is less than 0.060" after said parison is expanded against said mold.

16. The method according to claim 15, wherein each of said gaps is 0.010" to 0.050" after said parison is expanded against said mold.

17. The method according to claim 1, wherein said dilation element segments comprise a neck portion and a head portion, at least part of said neck portion extending across each of said gaps after said parison is expanded against said mold.

18. The method according to claim 1, wherein said parison is stretched a single time after said cutting, and said heating and stretching are done simultaneously with said heating of said parison and pressurizing said central opening.

19. The method according to claim 1, wherein said mold comprises cavities receiving said dilation element during said heating and pressurizing.

20. The method according to claim 1, wherein said cutting comprises mounting said parison on a mandrel in a computer-controlled cutting machine, and said cuts are made with a blade attached to a head in said cutting machine.

* * * * *

UNITED STATES PATENT AND TRADEMARK OFFICE
CERTIFICATE OF CORRECTION

| | | |
|---|---|---|
| PATENT NO. | : 8,764,705 B2 | Page 1 of 1 |
| APPLICATION NO. | : 13/696473 | |
| DATED | : July 1, 2014 | |
| INVENTOR(S) | : Eric R. Hennessy | |

It is certified that error appears in the above-identified patent and that said Letters Patent is hereby corrected as shown below:

On the Title Page

Item (12)

Change "Hennessey" to --Hennessy--

Item (75) <u>Inventors</u>

Change "Eric R. Hennessey" to --Eric R. Hennessy--

Signed and Sealed this
Twenty-first Day of October, 2014

Michelle K. Lee
*Deputy Director of the United States Patent and Trademark Office*